(12) United States Patent
Nuttall (10) Patent No.: US 7,390,305 B2
(45) Date of Patent: Jun. 24, 2008

(54) PEAK FLOW METER

(75) Inventor: Michael Nuttall, London (CA)

(73) Assignee: Trudell Medical International, London Ontario (CA)

( * ) Notice: Subject to any disclaimer, the term of this patent is extended or adjusted under 35 U.S.C. 154(b) by 96 days.

(21) Appl. No.: 11/377,710

(22) Filed: Mar. 16, 2006

(65) Prior Publication Data

US 2006/0217627 A1 Sep. 28, 2006

Related U.S. Application Data

(60) Provisional application No. 60/664,799, filed on Mar. 23, 2005.

(51) Int. Cl.
*A61B 5/02* (2006.01)

(52) U.S. Cl. ........................ 600/538; 600/529

(58) Field of Classification Search ........................ None
See application file for complete search history.

(56) References Cited

U.S. PATENT DOCUMENTS

| | | | |
|---|---|---|---|
| 471,389 A | 3/1892 | Lacey | |
| 599,746 A | 3/1898 | St. John | |
| 1,541,750 A | 6/1925 | Park | |
| 2,061,852 A | 11/1936 | Schweitzer | |
| 3,298,362 A | 1/1967 | Lippitt, Jr. et al. | |
| 3,559,638 A * | 2/1971 | Potter | 600/540 |
| 3,635,214 A | 1/1972 | Rand et al. | |
| 3,681,986 A | 8/1972 | Wyatt | |
| 3,719,083 A | 3/1973 | Morris et al. | |
| 3,720,202 A | 3/1973 | Cleary | |
| 3,722,278 A | 3/1973 | Young et al. | |
| 3,797,480 A | 3/1974 | Williams | |
| 3,826,247 A | 7/1974 | Ruskin et al. | |
| 3,862,628 A | 1/1975 | Williams | |
| 3,940,984 A | 3/1976 | Oram | |
| 3,958,565 A | 5/1976 | Wright | |
| 4,019,382 A | 4/1977 | El-Gammal | |
| 4,041,935 A | 8/1977 | Garbe | |
| 4,050,303 A | 9/1977 | Hemp et al. | |

(Continued)

FOREIGN PATENT DOCUMENTS

EP 0741995 11/1996

(Continued)

OTHER PUBLICATIONS

Advertisement of Vitalograph peak flow meter from Apr./May 1994 "Journal of Respiratory Care Practitioners".

(Continued)

*Primary Examiner*—Robert L Nasser
(74) *Attorney, Agent, or Firm*—Brinks Hofer Gilson & Lione (57) ABSTRACT

A peak flow meter is described with a body having a sample channel and at least one bypass channel. One of at least two flow range scales may be selected using a flow range selector to adjust the sensitivity of the peak flow meter. A flow range selection indicator provides visual reference as to which flow range scale has been selected. A peak flow calculator used in cooperation with zone indicators on the peak flow meter permits a user to customize the peak flow meter for that user's predicted personal best exhalation range.

18 Claims, 6 Drawing Sheets

U.S. PATENT DOCUMENTS

| | | | |
|---|---|---|---|
| 4,078,428 | A | 3/1978 | Baker et al. |
| 4,196,621 | A | 4/1980 | Beese et al. |
| 4,227,409 | A | 10/1980 | Bingler |
| 4,259,967 | A | 4/1981 | Vooren et al. |
| 4,287,775 | A | 9/1981 | Hutton |
| 4,292,853 | A | 10/1981 | Williams et al. |
| 4,294,262 | A | 10/1981 | Williams et al. |
| D263,166 | S | 2/1982 | Bushman |
| 4,421,120 | A | 12/1983 | Edwards, Jr. et al. |
| 4,533,137 | A | 8/1985 | Sonne |
| 4,638,812 | A | 1/1987 | Hakkinen |
| 4,640,293 | A | 2/1987 | Garbe et al. |
| 4,768,520 | A | 9/1988 | Varraux et al. |
| 4,944,306 | A | 7/1990 | Alvino |
| 4,967,596 | A | 11/1990 | Rilling et al. |
| 5,246,010 | A | 9/1993 | Gazzara et al. |
| 5,320,107 | A | 6/1994 | O'Brien |
| 5,540,234 | A * | 7/1996 | Lalui ............................ 600/538 |
| 5,565,630 | A * | 10/1996 | Shene ...................... 73/861.53 |
| 5,627,324 | A | 5/1997 | Shene |

FOREIGN PATENT DOCUMENTS

| | | |
|---|---|---|
| GB | 267933 | 6/1927 |
| GB | 1160669 | 8/1969 |
| WO | WO 91/11140 | 8/1991 |
| WO | WO 93/06778 | 4/1993 |
| WO | WO 93/07778 | 4/1993 |

OTHER PUBLICATIONS

Manual entitled "Peak Performance A Strategy for Asthma Self-Assessment", by Guillermo R. Mendoza, M.D., dated 1987.
Advertisement for "Assess Peak Flow Meter", believed to be published prior to Nov. 17, 1993.
Advertisement for "Personal Best Flow Meter", believed to be published prior to Nov. 17, 1993.
Advertisement for "Astech Peak Flow Meter", believed to be published prior to Nov. 17, 1993.
Photographs of "Pocketpeak" peak flow meter manufactured by Ferraris Medical Ltd. believed to be known or used prior to Nov. 17, 1993.
Photographs of "SPRI-O-Flow" peak flow meter manufactured by Spirometrics, Inc. believed to be known or used prior to Nov. 17, 1993.
Photographs of peak flow meter manufactured by Ferraro's Medical Ltd. believed to have been known or used prior to May 11, 1995.
Instruction manual for "SPIRA" peak flow meter believed to have been published prior to May 11, 1995.
Instruction manual for "ASSESS" peak flow meter manufactured by HealthScan Products, Inc., dated Aug. 1991.
Instruction manual for "Personal Best" peak flow meter manufactured by HealthScan Products, Inc. dated 1994.
Pamphlet entitled "Peak Flow Monitoring for Patients With Asthma", published by HealthScan Inc., dated 1990.
PCT International Search Report and Written Opinion dated Aug. 4, 2006 for Application No. PCT/IB2006/000587.
International Preliminary Report on Patentability dated Sep. 25, 2007 for Application No. PCT/IB2006/000587.

* cited by examiner

PEAK FLOW METER

CROSS-REFERENCE TO RELATED APPLICATIONS

This application claims the benefit of U.S. provisional application No. 60/664,799, filed Mar. 23, 2005, the entirety of which is hereby incorporated by reference.

BACKGROUND

Peak flow meters are used for measuring the peak air flow of a patient's exhalation. Peak flow meters permit physicians to track changes in the patient's respiratory condition and diagnose potential or existing breathing problems. Patients may also use peak flow meters outside of a doctor's office to monitor their own condition on a regular basis.

A challenge for manufacturers of peak flow meters is to provide a reliable and accurate device that consumers can afford. Accuracy, particularly in lower flow ranges, can be a problem in full range peak flow meters, such as those that provide measurements over the range of approximately 20-800 liters per minute (L/min). Also, current peak flow meter performance guidelines related to the accuracy of how peak flow meters respond to certain defined impulse waveforms (representative of the initial impulse of airflow into a peak flow meter expected from a patient) may be difficult for existing peak flow meters to achieve.

Accordingly, there is a need for a peak flow meter that provides detailed, accurate information and is simple to set up and use.

SUMMARY

The embodiments described below relate to a peak flow meter adaptable for use to accurately measure peak flow of exhaled air of a patient in at least a high flow configuration and a lower flow configuration. According to a first aspect of the invention, a peak flow meter is described having a body to accommodate the flow of exhaled air in an indicator associated with the body. The indicator is moveable along a path relative to the body to a position along the body that represents a peak flow of air exhaled through the body. A first flow rate scale is positioned on the body adjacent the path and a second flow rate scale is positioned on the body adjacent the path. A flow range selector is moveably positionable on the body to a first position or a second position. In the first position, the movement of the indicator in response to the flow of exhaled air will conform to the first flow rate scale. In the second position, the movement of the indicator in response to the flow of exhaled air will conform to the second flow rate scale.

Other aspects of the invention may include a plurality of channels in the body. One channel may be a sample channel for receiving a portion of air exhaled into the peak flow meter. The sample channel may be positioned adjacent a first bypass channel and a second bypass channel, each receiving a share of the remainder of the exhaled air. In one embodiment, the flow range selector may block at least one of the first and second bypass channels when the flow range selector is in the second position. Other embodiments, the flow range selector may include a flow range selection indicator visible outside the body. The flow range selection indicator may be configured to indicate which of the first and second flow rate scales the peak flow meter is currently configured to use.

Further aspects and advantages of the invention are discussed below in conjunction with the preferred embodiments.

DETAILED DESCRIPTION

FIGS. 1-5 illustrate a peak flow meter 10 according to an embodiment of the present invention. The peak flow meter 10 may include a body 12 having a mouthpiece portion 14 with an inlet 16 at one end, and an outlet 18 at an opposite end. The peak flow meter 10 also has a grip region 20 for a patient to hold on to while using the device and a finger stop 21 protruding from the body 12 parallel to the grip region 20. The grip region 20 may be a raised portion of the body shaped in an angular manner other geometric form to allow an easy and secure grip. The grip 20 may be smooth or textured. Also, the grip may be an integrally molded part or a separately attached or adhered material. Similarly, the finger stop 21 may be a raised ridge, integrally molded or attached to the body. The finger stop may be sized to prevent a user's fingers from inadvertently encroaching on the path of the indicator 22.

Figure 5:
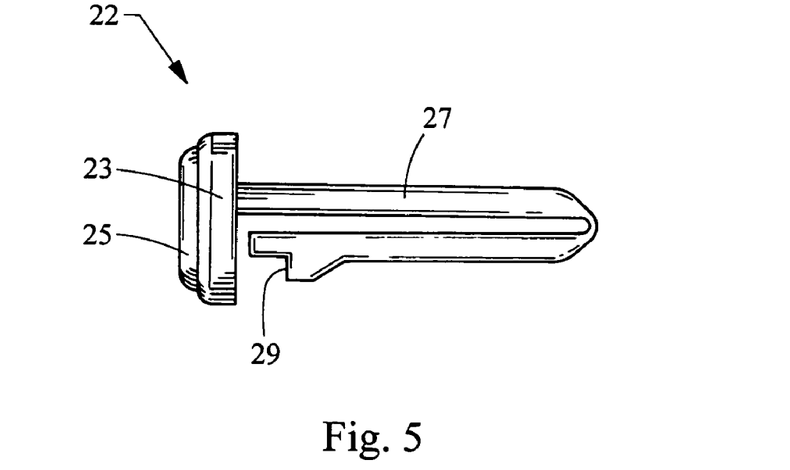
FIG. 5 is an enlarged view of a peak flow indicator suitable for use in the peak flow meter of FIG. 1.
Figure 6:
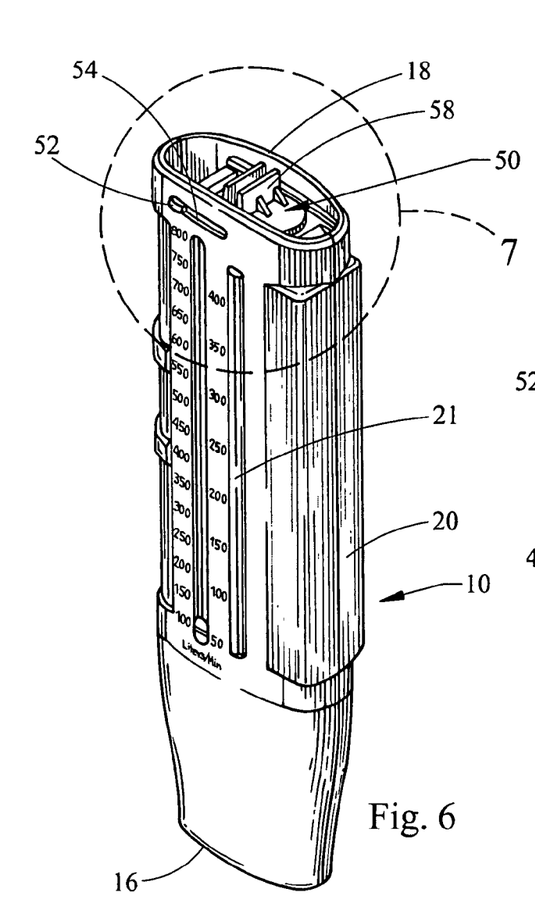
FIG. 6 is a perspective view of the peak flow meter of FIG. 1.
Figure 7:
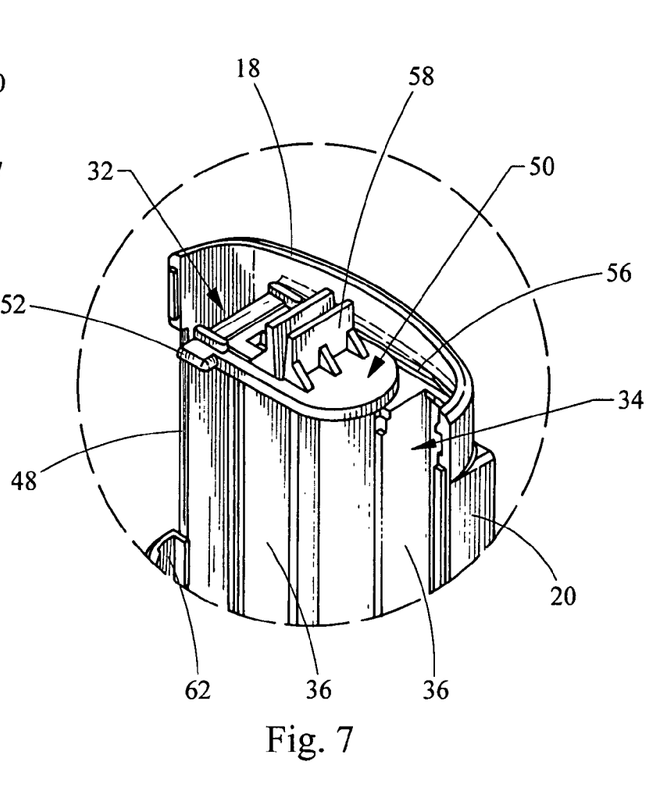
FIG. 7 is an enlarged sectional view taken along the line A of FIG. 6.
Figure 8:
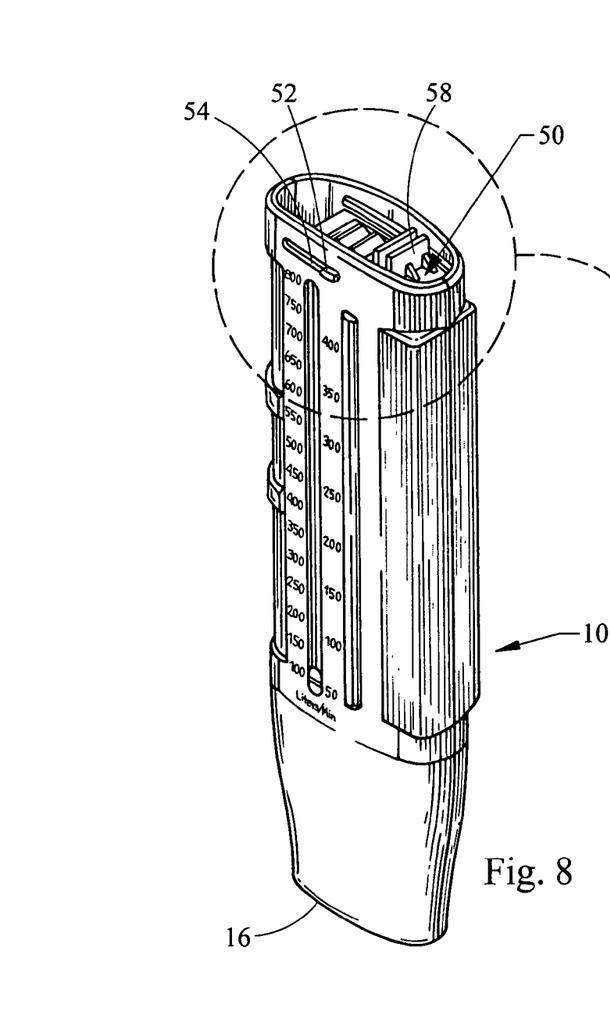
FIG. 8 is a perspective view of the peak flow meter of FIG. 1 with the flow range selector in a low flow configuration.
Figure 9:
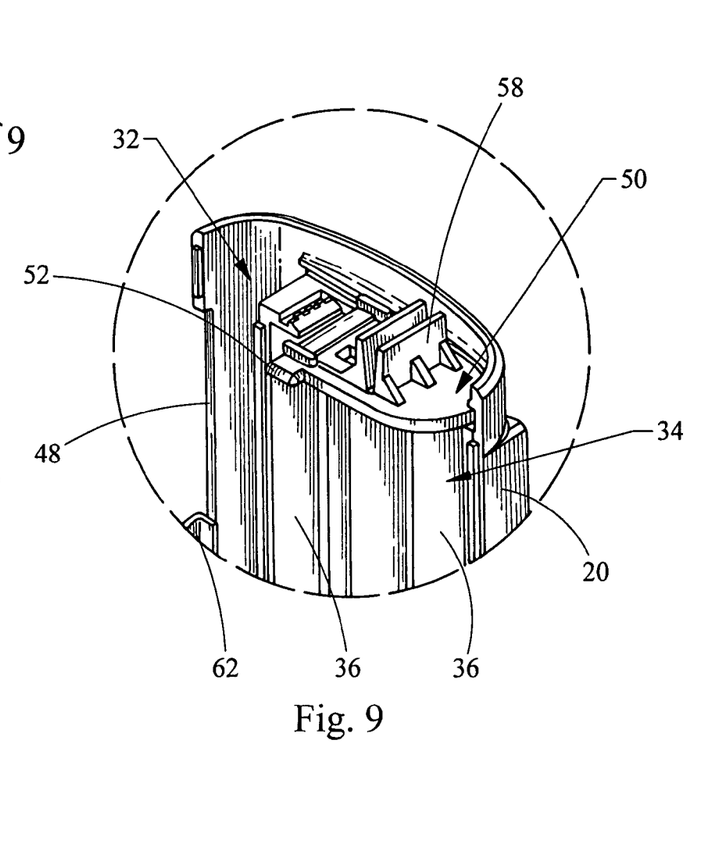
FIG. 9 is a sectional view taken along line B of FIG. 8.
Figure 10:
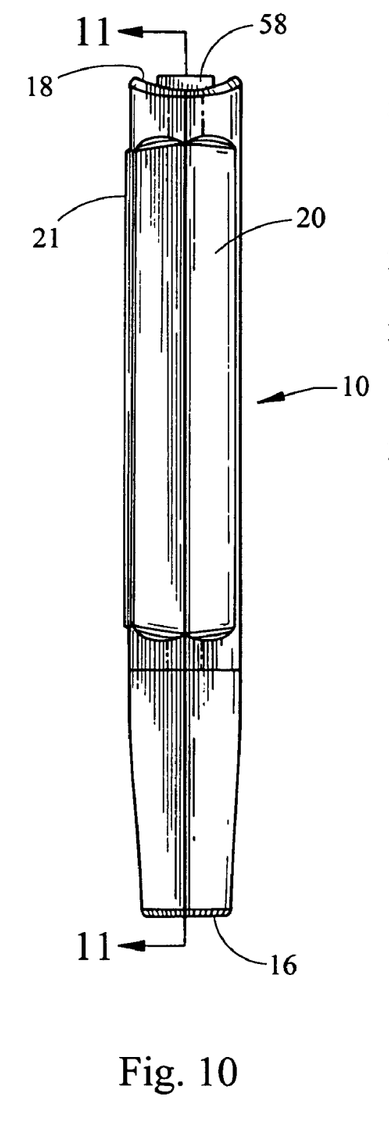
FIG. 10 is a side view of the peak flow meter of FIG. 8.
Figure 11:
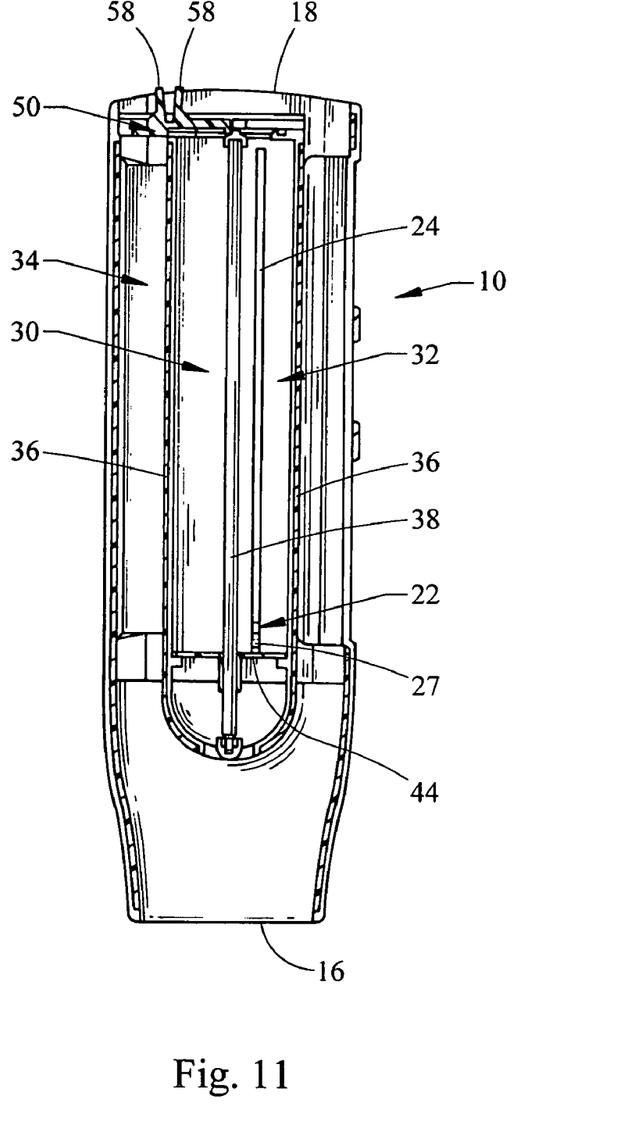
FIG. 11 is a sectional view taken along line 11-11 of FIG. 10.

A peak flow indicator 22 is slidably mounted in a slot 24 formed in the body 12. FIG. 5 illustrates one embodiment of the indicator 22. The indicator may include a head portion 23 having a ridge 25 or other user accessible contact portion. A stem 27 is designed to extend into the slot 24 through the body 12 of the peak flow meter 10 and includes a contact ridge 29 configured to engage the underside of the body, inside the slot 24. The stem 27 may be bent in a u-shape such that the stem is biased outwards toward the opposing edges of the slot 24 and provides a friction fit in the slot sufficiently tight to hold the indicator in position when not in contact with a user finger or the piston 44 discussed below, but loose enough to allow movement of the indicator 22 along the slot when acted on by the piston 44 or a finger. The slot 24 defines a path for the indicator 22 that may extend longitudinally along the body along between the inlet 16 and outlet 18. A pair of scales 26, 28 are positioned adjacent to, and on opposite sides of, the slot 24.

Figure 2:
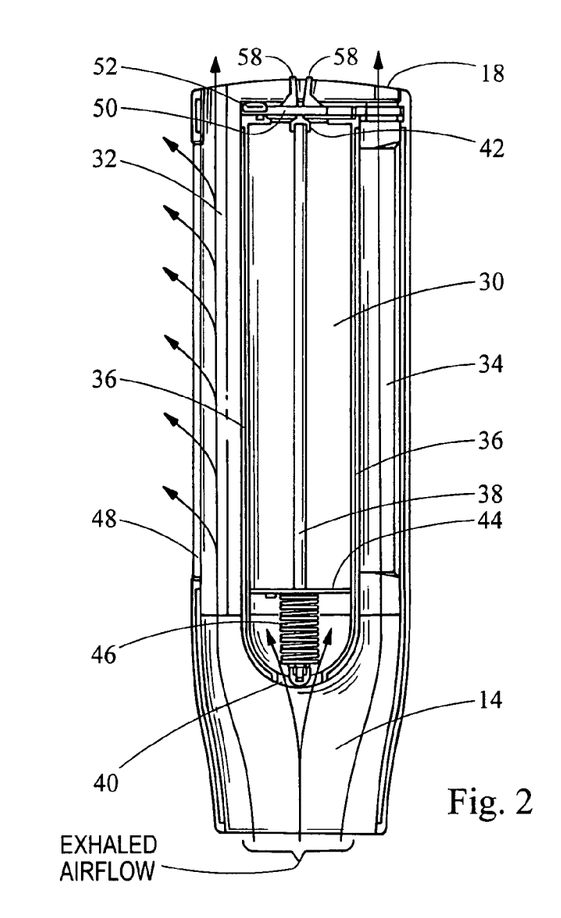
FIG. 2 is a sectional view of FIG. 1 showing the interior of the peak flow meter of FIG. 1.
Figure 3:
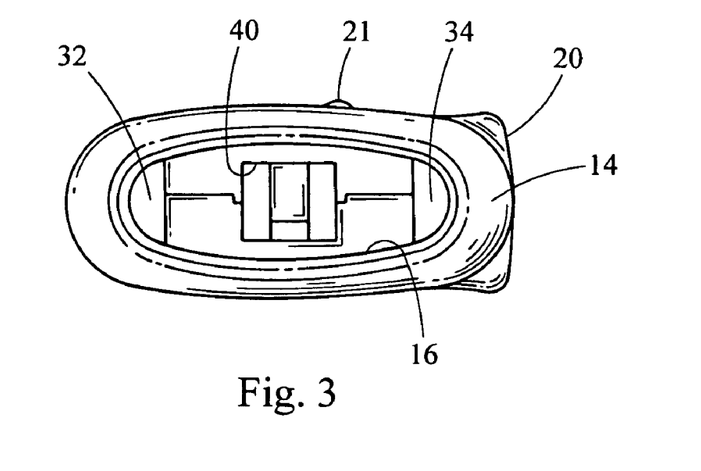
FIG. 3 is an inlet end view of the peak flow meter of FIG. 1.
Figure 4:
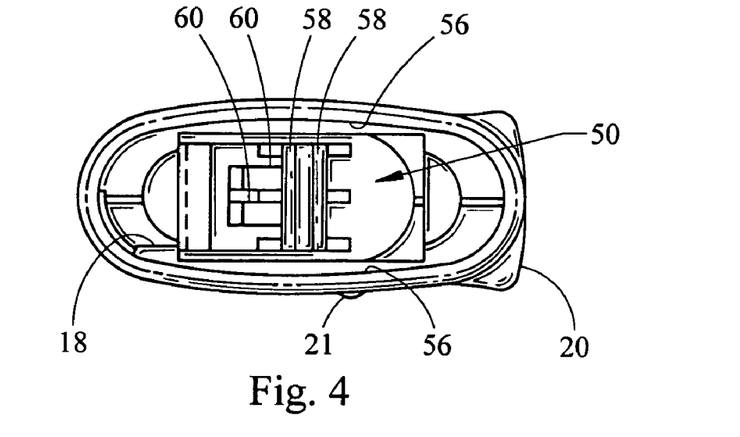
FIG. 4 is an outlet end view of the peak flow meter of FIG. 1.

Inside the peak flow meter 10, as shown in FIG. 2, the single channel defined by body 12 at the mouthpiece portion 14 divides into three separate channels: a sample channel 30, a first bypass channel 32 and a second bypass channel 34. A pair of walls 36 extending longitudinally along the inside of the body separates the three channels. A shaft 38 extends from the entrance 40 to the sample channel 30 to the exit end 42 of the sample channel 30 located near to the outlet 18 of the peak flow meter 10. A piston 44 is slidably mounted on the shaft 38. The piston 44 may be constructed to substantially match the cross-sectional area of the sample channel 30 so that little or no exhaled air entering into the sample channel can pass between the walls 36 and the piston 44. In other embodiments, the dimensions of the piston relative to the cross-sectional area of the sample channel may be smaller such that more exhaled air may pass around the edges of the piston. Alternatively, the walls 36 dividing the channels inside the body 14 may taper outward from the entrance end 40 to the exit 42 so that there is gradually more space between the edges of the piston and the walls of the sample channel as the piston travels down the shaft 38.

A biasing member 46, such as a spring, may be coaxially positioned around the shaft 38, attached to the piston at one end and attached to the shaft 38 or other portion of the body 12 at the opposite end. As shown in FIG. 2, the biasing member 46 may be a linear spring arranged to operate in tension mode so that, at rest, the tension of the spring maintains the piston 44 in an initial position near the entrance 40 of the sample channel. In alternative embodiments, more than one tension spring may be used, a compression spring positioned between the exit wall 42 and piston 44 may push the piston toward the entrance, or a combination of tension and compression springs may be used.

The first bypass channel 32 extends from the mouthpiece portion 14 to the outlet 18 in parallel with the sample channel 30. At least one opening or slot 48 extends along the body 12 and into the first bypass channel 32 so that a portion of the air exhaled into the mouthpiece portion 14 and traveling into the first bypass channel may vent from the peak flow meter 10. The slot 48 may be a continuous slot extending along the first bypass channel or a series of evenly or unevenly spaced openings. In yet other embodiments, the size of the slot 48 or openings may change along the length of the peak flow meter.

The second bypass channel 34 extends parallel to the sample channel 30 and first bypass channel 32. The second bypass channel 34 may be formed without openings or slots along its length and only provide for an exit at the outlet 18 of the peak flow meter. Alternatively, the second bypass channel may have slots or openings of the same or different size and pattern as in the first bypass channel. Although the cross-sectional areas of the bypass channels 32, 34 may be the same, the cross-sectional areas may differ in other embodiments to accommodate different ranges of sensitivity. Although two bypass channels that extend the length of the peak flow meter and are parallel to the sample channel are shown, other configurations and numbers of bypass channels may be used.

The size of the bypass channels 32, 34 and sample channel 30, along with the size and position of the slot 24 in the sample channel and slot 48 in the first bypass channel are empirically designed such that the force of exhaled air into the peak flow meter 10 at the inlet 16 moves the piston 44 along the shaft 38 against the tension force of the spring 46, along with the indicator 22 in the slot 24 to a position along the appropriate scale 26, 28 corresponding to the peak flow of the exhale of air. Thus, the slots 24, 48 and channels 30, 32, 34 are designed to tailor the response of the peak flow meter to a patient's forceable exhalation such that the indicator's 22 movement conforms to a selected one of the two scales. Additionally, the peak flow meter's sensitivity to the impulse waveforms of exhaled air may be designed to accommodate EN 13826 PFM standards and allow a maximum backpressure per liter flow second of 2.5 cm $H_2O$. An advantage of the bypass channel configuration is a reduction of piston overshoot in response to rapid-rise exhalation waveforms.

As best shown in FIGS. 6-11, a flow range selector 50 is slideably mounted adjacent the outlet 18 of the peak flow meter. The flow range selector 50 may include a flow range selection indicator 52 positioned in a slot 54 in the front of the peak flow meter adjacent the outlet end 18. Inside the outlet 18 of the peak flow meter 10, guide grooves 56 retain the flow range selector 50 in a slideably moveable arrangement against the end of the walls 36 extending through the interior of the peak flow meter. A handle 58 on the flow range selector 50 extends outwardly towards the open outlet end 18 so that a user may adjust the position of the flow range selector.

In a first position, as shown in FIGS. 1-6, the flow range selector is in a high flow position that permits air to exit the peak flow meter through both the first and second bypass channels 32, 34 and, through vents 60 in the flow range selector 58, allows air to exit the sample channel as well. In this first position for the flow range selector 50, the flow range selection indicator 52 is positioned directly above the high flow scale which may range from approximately 100 liters per minute to 800 liters per minute. This is a scale range typical of patients capable of producing higher flows such as adults.

Referring to FIGS. 7-10, the flow range selector 50 may be moved by grasping the handle 58 and sliding it so that one end covers the second bypass channel. In this second position of the flow range selector, the second bypass channel 34 is substantially blocked and exhaled air is prevented from passing through that channel. By blocking the second bypass channel 34, the peak flow meter 10 is configured for higher sensitivity and is more responsive to lower flow exhalations, such as those of children. In the second position, the flow range selection indicator 52 now rests above the lower flow rate scale 28, which in this example ranges from 50-400 liters per minute. The position of the flow rate indicator alerts the user of the scale to which the movement of the indicator 22 will now conform.

Alternate embodiments for the flow range selector are contemplated. Although shown as positioned adjacent the outlet end of the peak flow meter, the flow range selector may be positioned at the inlet of the peak flow meter or at some intermediate position between the inlet and outlet. Also, rather than separate indicator 52 and handle 58 elements of the flow range selector 50, the two could be combined. One version of the combined handle and indicator may be to eliminate the slot 54 and extend the handle 58 further out from the outlet and align the protruding handle so that it extends out from the peak flow meter aligned with the scale being selected. The handle in this embodiment may have an L-shape with the foot of the L oriented in the direction of the scale side of the body for easier visual recognition. In another embodiment, the handle 58 may be eliminated and the indicator 52 extended out of the body with a slider attachment, for example similar to that of the indicator 22 so that the range selection and indication may both be accomplished on the scale side of the body 12. In another embodiment, the flow range selector may be a removable plug, with or without a tether connection to the body, sized to block at least one bypass channel. In yet other embodiments, a rigid flap of material may be pivotally connected to the peak flow meter so that the rigid flap may be rotated into and out of a bypass channel blocking position.

Figure 1:
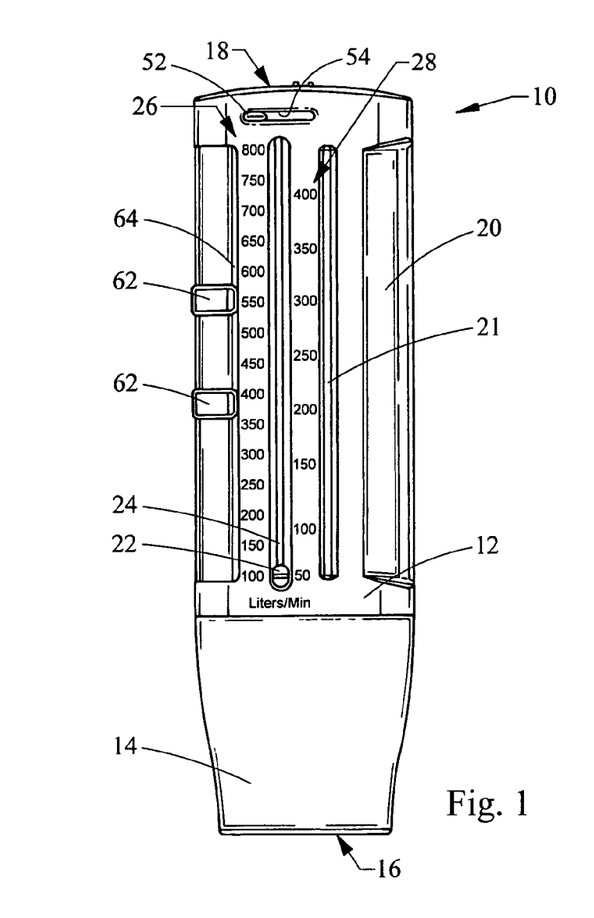
FIG. 1 is a front view of an embodiment of a peak flow meter according to the present invention.

Referring again to FIG. 1, the peak flow meter 10 may also include one or more adjustable zone indicators 62 that may be manually adjusted along the body of the peak flow meter parallel to the scales 26, 28. In the embodiment of FIG. 1, the zone indicators 62 are slideably engaged at a first end in a friction fit groove 64 extending parallel to the scales 26, 28 on the front of the peak flow meter. The other end of the zone indicator may be frictionally engaged with the slot 48 in the side of the peak flow meter. The zone indicators 62 may be used by a patient or a physician to label particular percentage values of personal best peak flow performance. For example, one of the zone indicators may be positioned at a point along the scale that represents 80% of the predicted personal best peak flow for that particular patient. The second of the zone designators may be positioned at a point along the scale representing the 50% value of the patient's predicted personal best peak flow.

Figure 12:
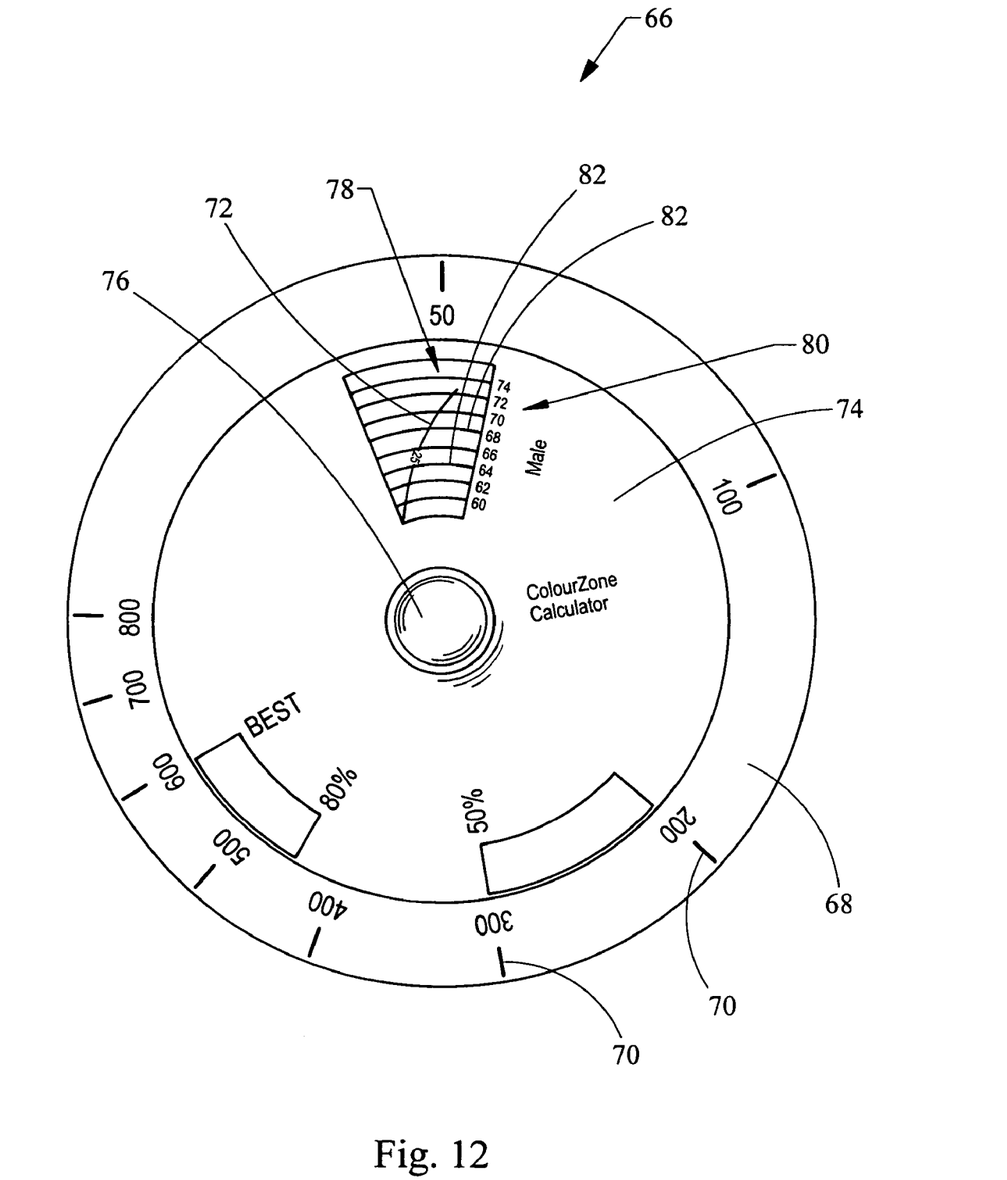
FIG. 12 illustrates a zone calculator for use with the peak flow meter of FIGS. 1-11.

Referring to FIG. 12, a zone calculator 66 is shown for use in setting the reference designators 62 at the appropriate positions along the scales 26, 28 on the peak flow meter 10. The calculator 66 may comprise a base disk 68 having peak flow range indicia 70 and age reference curves 72 imprinted on it. A range disk 74 having a lesser diameter than the base disk 68 is held in a rotatably adjustable configuration against the base disk 68 by a central rivet member 76. The range disk 74 includes three fixed length ranges, preferably having different color bands or other visible markings identifying three separate zones separated by an 80% predicted flow point and a 50% predicted flow point. In one embodiment, the zone representing 80% or better is marked in green, the zone representing 50%-80% is in yellow, and less than 50% is indicated in red.

Additionally, the range disk 74 includes a window 78 permitting a user to see through the range disk 74 to the age curve 72 marked on the base disk. A height scale 80 is arranged along the edge of the window 78 and, in order to provide better visual guidance, reference lines 82 may be printed across the window so that the intersection point of a particular height and the age curve may be readily determined. Once the appropriate age curve on the base disk 68 is lined up in the window with the height designations on the upper disk 74 the user may then determine the 80% and 50% predicted best peak flow in comparison the scale on the outer edge of the lower disk so that each of the zone indicator 62 on the peak flow meter may be placed in the appropriate position for that user. In one embodiment, the scale on the base disk 68 includes reference indicia that are spaced logarithmically such that a constant angular distance along that scale corresponds to a constant percentage change.

A method of using the peak flow meter set forth above is now described. A user or physician first selects the appropriate flow range, based on the predicted peak flow for the user. The predicted peak flow may be obtained with the calculator 66 based on the age and height data on the calculator 66, or may be based on historical data already known regarding the user. The range of the peak flow meter may then be adjusted by grasping the handle 58 of the flow range selector 50 and moving the selector until the indicator 52 shows that the desired scale has been selected. In the embodiments shown, either a high flow range, here 100-800 liters per minute, or a low flow range, 50-400 liters per minute are available options.

As a baseline for future measurements, the user may then take an initial peak flow measurement with the peak flow meter. In order to maintain the appropriate levels of cleanliness and sanitation when the peak flow meter is used by different patients in a physician's office, a disposable cardboard or plastic adaptor (not shown) may be used at the mouthpiece end 14 of the peak flow meter. This adapter may be any one of a number of adaptors available and may be held in place through friction fit. One suitable supplier of mouthpiece adapters is SDI Diagnostics of Easton, Mass. Once the mouthpiece adapter, if desired, is in place, the user may hold the peak flow meter in the grip region 20. The grip region in combination with the finger stop 21 allow a user to securely hold the device without risking blockage of the slot 24 or interference of the movement of the indicator 22 along the slot 24.

Grasping the grip region 20, the user exhales forcibly into the inlet 16. The burst of exhaled air will push the piston 44 which, in turn, pushes the stem 27 of the indicator 22. The indicator stops at a point along the slot 24 where the force exerted on the piston 44 by the spring 46 substantially equals the force of the exhaled air remaining in the sample channel 30. As discussed above, in order to obtain the preferred response, the slots in the sample and first bypass channels, along with the configuration of bypass channels and sample channel allow empirically determined amounts of exhaled air to move along or escape the peak flow meter so that the indicator's position conforms to the selected scale. The frictional fit of the indicator 22 in the slot 24 keeps the indicator in place when the piston 44 is retracted by the spring 46. The peak flow for the patient is represented by the indicator. Once the position of the indicator is identified along the previously selected scale, as shown by the flow range selection indicator 52, the user can return the indicator to its initial position by manually sliding the indicator back to the bottom of the slot 24. Based on the personal best reading just obtained, and on the calculated personal best exhalation from the calculator 66, the physician or user may then set the location of the zone indicators 62 so that the user is aware of how future uses of the peak flow meter compare to the expected range for that user.

It is contemplated that, in other embodiments, the linear scales 26, 28 shown in FIG. 1 may be replaced with logarithmic scales such that the zone designator 62 may be a single piece that accurately reflects the zones regardless of position along the logarithmic scale. In order to implement a logarithmic scale embodiment, the slots 28, 48 and bypass channels 32, 34 may be configured to include gradually wider openings to permit more venting of air from the peak flow meter such that less pressure is applied to the piston inside the peak flow meter.

Alternatively, a variable rate spring may replace the linear spring used in the embodiment described above. The variable rate spring may be used alone, or in combination with adjusting the slot sizes to achieve correspondence of the logarithmic scales to movement of the indicator. The spring coil diameter may be gradually increased, the spring coil thickness changed along the spring's length, or a combination of different size springs may be combined so that the force varies non-linearly or logarithmically. Another technique is the use of a flexible piston that flexes to permit greater amounts of air to pass as the force of the air against it increases. Additionally, the shaft carrying the piston 44 may be constructed such that the friction between the piston and the shaft increases as the indicator is pushed further down the shaft. These techniques may be used individually or in combination with each other so that the indicator's response to a peak flow of exhaled air conforms to a chosen scale.

In yet other embodiments, additional vents or slots may be placed in the body of the peak flow meter allowing exhaled air to exit from the sample channel as well. The sample channel may vent to the ambient air outside the peak flow meter or may indirectly vent to the ambient air through openings or slots in the walls between the sample and bypass channels inside the peak flow meter itself.

The body of the peak flow meter 10 may be constructed out of two pieces, into which the shaft, spring and piston are placed prior to joining the two piece body together. In one embodiment, the body, zone indicators and flow range selector may be constructed of ABS plastic. The shaft and spring may be constructed of stainless steel, the indicator of polypropylene (PP) and the piston of PTFE, PP or polyethylene. Other materials, including plastics or metals, are contemplated. The pieces of the body may be joined by ultrasonic welding, adhesives or other known processes. The shaft may be a solid, ground stainless steel or other materials. The shaft, after assembly with the spring and piston, may be a snap fit, welded, threaded into, or otherwise connected and aligned within the sample channel of the body. The spring may be attached to the shaft or body via any of a number of attachment techniques, including gluing or heat staking.

A peak flow meter has been described having a bypass channel design to improve accuracy and a selectable flow range. It is intended that the foregoing detailed description be regarded as illustrative rather than limiting, and that it be understood that the following claims, including all equivalents, are intended to define the scope of this invention.

I claim:

1. A peak flow meter comprising:
   a body for accommodating a flow of exhaled air therethrough;
   an indicator associated with the body and movable along a path relative to the body to a position along the body, the position related to a peak flow of air exhaled through the body;
   a first flow rate scale positioned on the body adjacent the path;
   a second flow rate scale positioned on the body adjacent the path;
   a flow range selector movably positionable on the body in a first position, wherein movement of the indicator in response to the flow of exhaled air conforms to the first flow rate scale, or in a second position, wherein movement of the indicator in response to the flow of exhaled air conforms to the second flow rate scale; and
   wherein the flow range selector is positioned to block a portion of the flow of exhaled air when in the second position.

2. The peak flow meter of claim 1 wherein the path comprises a slot in the body and the indicator is slidably mounted in the slot.

3. The peak flow meter of claim 2 further comprising a piston slidably mounted within the body engaging said indicator.

4. The peak flow meter of claim 1 wherein the body defines a sample channel, a first bypass channel and second bypass channel.

5. The peak flow meter of claim 4 wherein the flow range selector blocks at least one of the first and second bypass channels in the second position.

6. The peak flow meter of claim 5 wherein said sample channel is positioned at an angle relative to at least one of the first or second bypass channels.

7. The peak flow meter of claim 4 wherein the sample channel is aligned parallel to at least one of the first or second bypass channels.

8. The peak flow meter of claim 1 wherein the flow range selector further comprises a flow range selection indicator visible outside of the body.

9. The peak flow meter of claim 8, wherein the flow range selection indicator is configured to indicate which of the first flow rate scale or second flow rate scale the peak flow meter is configured to use.

10. The peak flow meter of claim 8, wherein the flow range selection indicator is positioned adjacent the first flow rate scale when the flow range selector is in the first position and the flow range selection indicator is positioned adjacent the second flow rate scale when the flow range selector is in the second position.

11. The peak flow meter of claim 1 wherein the flow range selection indicator and the flow range selector are constructed from a unitary piece of material.

12. The peak flow meter of claim 1 wherein the first flow rate scale comprises a nonlinear scale.

13. A peak flow meter comprising:
    an inlet for receiving a flow of exhaled air into a hollow body;
    an outlet for venting at least a portion of the flow of exhaled air;
    a piston movably positioned inside the hollow body for moving a peak flow indicator along a path in response to the flow of exhaled air;
    at least two scales positioned adjacent the path, each of the at least two scales demarcating a different flow range;
    a flow range selector movably positionable on the body at a first position, wherein movement of the peak flow indicator in response to the flow of exhaled air conforms to a first of the at least two scales, or at a second position, wherein movement of the indicator in response to the flow of exhaled air conforms to a second of the at least two scales; and
    wherein the flow range selector is positioned to block a portion of the flow of exhaled air when at the second position.

14. The peak flow meter of claim 13 wherein the peak flow meter further comprises a flow range selection indicator visible outside of the body.

15. The peak flow meter of claim 14, wherein the flow range selection indicator is configured to indicate which of the at least two scales the peak flow meter is configured to use.

16. The peak flow meter of claim 13, wherein the hollow body comprises an integral grip region for holding the peak flow meter.

17. The peak flow meter of claim 16, wherein the hollow body comprises a finger stop positioned between the integral grip region and the peak flow indicator, the finger stop comprising a raised material located on the hollow body.

18. The peak flow meter of claim 13 further comprising at least one bypass channel located in the hollow body, the bypass channel oriented to direct a portion of the flow of exhaled air away from the piston.

* * * * *